US012642835B2

(12) United States Patent
Harti

(10) Patent No.: US 12,642,835 B2
(45) Date of Patent: Jun. 2, 2026

(54) LONG TERM TREATMENT OF ATOPIC DERMATITIS

(71) Applicant: LEGACY HEALTHCARE (SWITZERLAND) SA, Epalinges (CH)

(72) Inventor: Saad Harti, Epalinges (CH)

(73) Assignee: LEGACY HEALTHCARE (SWITZTERLAND) SA, Epalinges (CH)

( * ) Notice: Subject to any disclaimer, the term of this patent is extended or adjusted under 35 U.S.C. 154(b) by 0 days.

(21) Appl. No.: 18/240,638

(22) Filed: Aug. 31, 2023

(65) Prior Publication Data

US 2025/0073300 A1     Mar. 6, 2025

(51) Int. Cl.
| | |
|---|---|
| *A61K 36/8962* | (2006.01) |
| *A61K 36/185* | (2006.01) |
| *A61K 36/752* | (2006.01) |
| *A61K 36/77* | (2006.01) |
| *A61P 17/00* | (2006.01) |

(52) U.S. Cl.
CPC ........ *A61K 36/8962* (2013.01); *A61K 36/185* (2013.01); *A61K 36/752* (2013.01); *A61K 36/77* (2013.01); *A61P 17/00* (2018.01)

(58) Field of Classification Search
None
See application file for complete search history.

(56) References Cited

FOREIGN PATENT DOCUMENTS

WO     WO 2012/140013     * 10/2012

OTHER PUBLICATIONS

Liu, JiaWei, et al. Journal of the American Academy of Dermatology. Hair and Nail Disorders. 74(5), supplement 1, AB132, May 2016.
Chopra R, Silverberg JI. "Assessing the severity of atopic dermatitis in clinical trials and practice". Clinics in Dermatology. 36:606-615, Sep. 2018.
Simpson, Eric, et al. "The Validated Investigator Global Assessment for Atopic Dermatitis (vIGA-AD): The development and reliability testing of a novel clinical outcome measurement instrument for the severity of atopic dermatitis". J AM Acad Dermatol. 83(3):839-846, Sep. 2020.
Leshem, Y. A., et al. "What the Eczema Area and Severity Index score tells us about the severity of atopic dermatitis: an interpretability study." The British journal of dermatology. 172(5), Jan. 2015.
Finlay, A.Y., Khan, G.K. "Dermatology Life Quality Index (DLQI)—a simple practical measure for routine clinical use." Clinical and experimental dermatology. 19: 210-216, Sep. 1993.
Braun, C. et al., "Pathophysiology of atopic dermatitis and other atopic diseases: is a global approach possible." Annals of Dermatology and Venereology. 147: 11S4-11S11, Nov. 2020.
Eichenfield, Lawrence F. et al. "Therapeutic education in atopic dermatitis: A position paper from the International Eczema Council." JAAD international. 3:8-13, Mar. 2021.
Newsom, Megan et al. "New and Emerging Systemic Treatments for Atopic Dermatitis." Drugs. 80(11):1041-1052, Jun. 2020.
Katoulis, Alexandros C et al. "Efficacy and Safety of a Topical Botanical in Female Androgenetic Alopecia: A Randomized, Single-Blinded, Vehicle-Controlled Study." Skin appendage disorders. 4:160-165, Aug. 2017.

* cited by examiner

*Primary Examiner* — Michael V Meller

(74) *Attorney, Agent, or Firm* — Harness Dickey & Pierce P.L.C.

(57)     ABSTRACT

The invention relates to methods of treatment and/or prevention of an inflammatory skin disease in a subject, wherein the therapeutic effects persist for at least 24 weeks or more after the last administration of the composition of the invention. Also disclosed are kits and methods of treating and/or preventing an inflammatory skin disease using said composition.

15 Claims, 1 Drawing Sheet

LONG TERM TREATMENT OF ATOPIC DERMATITIS

FIELD OF THE INVENTION

The invention relates to methods of treatment and/or prevention of an inflammatory skin disease in a subject, wherein the therapeutic effects persist for at least 24 weeks or more after the last administration of the composition of the invention. Also disclosed are kits and methods of treating and/or preventing an inflammatory skin disease using said composition.

BACKGROUND OF THE INVENTION

Atopic dermatitis (AD) is the most common chronic inflammatory skin disease, with a lifetime prevalence and substantial effects on quality of life. The most frequently observed symptoms of atopic dermatitis are excessive skin dryness and itching, exfoliation, redness, skin irritation, exudations, swelling of the affected skin areas, spots, rash, and blisters with watery secretion. *Staphylococcus aureus* is often being observed to colonize AD skin. The disorder affects people of all ages and ethnicities, has a substantial psychosocial impact on patients and relatives, and is the leading cause of the global burden from skin disease.

The causes of AD are multifactorial and characterized by a complex interplay of genetic, environmental, and immunological factors. This is believed to underlie the extreme clinical variety, mode of onset, and phenotypes observed in AD patients. Hence the disease may develop as persistent forms from childhood to late onset forms in adulthood or even in the elderly.

For many years, AD has been primarily considered as a childhood disease, this probably being explained by its prevalence in children. Hence, atopic dermatitis affects up to 20% of children and 10% of adults in high-income countries, based on annual self-reported prevalence estimates. In 2010, 230 million people worldwide were estimated to have eczema, with reports that the condition was the non-fatal skin disorder with the highest disease burden. Data on disease severity are scant but, in a multinational survey, 10-20% of adult patients with atopic dermatitis reported severe disease.

Although the prevalence of atopic dermatitis has plateaued in many high-income countries, it continues to increase in low-income and middle-income countries. The striking increase in prevalence over the past 30 years suggests that environmental factors are important, and the so-called hygiene hypothesis is frequently discussed as a possible explanation. Other evidence supporting the importance of environmental factors in AD prevalence includes urban-rural gradients with a reduced prevalence in farming households and a low prevalence in areas with high humidity, temperature, and ultraviolet light exposure. Concerning ethnicity, a higher prevalence was reported in the US in African American individuals (17%) than in white people (11%), with similar findings for black Caribbean children compared with white children in UK studies. However, it should be kept in mind that substantial variations in diagnostic criteria used to identify AD are still omnipresent in clinical practice. This leads to challenges due to the probable differences in underlying physiopathologies (genetic factors, others) and disease evolution stages at patient first visit, explaining therefore the great variability observed in patients outcomes according to the choice of treatments of first intention.

Hence, genetic factors involved in the innate and adaptive immune systems as well as proteins that regulate the terminal differentiation of keratinocytes may be associated with the disease and probably play a crucial role in AD etiopathogenesis, as confirmed by the evidence of a family predisposition. Recently, new insights into the pathophysiology of the development of AD focused on an important role of abnormalities in epidermal lipid layer as well as neuroimmune interactions and microbial dysbiosis modifying the protective acidic mantle of the skin and favoring infections. Eventually, like in other chronic inflammatory diseases, oxidative stress also plays an important pathogenetic role, but our understanding is still incomplete, at least concerning in vivo data, because of limitations of available literature.

Among the main proven factors that contribute to defining atopic dermatitis, and which translate into targets for the currently used or development of future therapeutic tools the present Inventors found: a) inflammation, b) itching, c) an alteration in skin barrier permeability, d) an impact of the skin microbiome, and d), in more severe cases, the presence of a local or systemic immune dysregulation favoring an epidermal barrier disruption.

Dysfunction of the epidermal barrier and type 2 immune overreaction, the latter resulting or not from genetic predispositions, are known to play a reciprocal role in the pathogenesis of AD. Due to AD complexity and heterogeneity, both on a clinical and physiopathological point of view, the primum movens of AD patient care is far today from being fully unanimous.

The general practice tends towards the use in the first place of local treatments (emollients, dermocorticoids, topical calcineurin inhibitors) and in the event of failure in moderate to severe forms, to switch to phototherapy, immunosuppressants such as cyclosporine, methotrexate, azathioprine, mycophenolate mofetil and dupilumab, these treatments also demonstrating different levels of success. This explains why translational research is currently developing new targeted small molecules and biologic therapies especially for moderate-to-severe disease. Most of these new therapies are still under clinical investigation including microbiota replacement, new phosphodiesterase 4 (PDE4) inhibitors, specific antibodies targeting e.g., skin alarmins, histamine, substance-P or P2X3 receptors, Ig-E, various cytokines or their receptors (IL-25, IL-33, IL-1a, IL-22, IL-17C, IL-31, IL-4(&R), IL-13(&R), -5(&Ra)), and eventually systemic immunosuppressants such as JAK Inhibitors. However, some of these new treatments are not without raising some concerns related to known side-effects, and they will therefore merit serious evaluations before being fully authorized to prescription, in particular to young patients.

There is high unmet medical need for a treatment which is both, safe enough not to warrant drug holidays, and which efficacy persists beyond treatment interruption.

SUMMARY OF THE INVENTION

This object has been achieved by providing a method of treatment and/or prevention of an inflammatory skin disease in a subject, said method comprising administering a composition comprising, as active ingredients, effective amounts of an extract of *Allium* species, an extract of *Citrus* species, an extract of *Paullinia* species and an extract of *Theobroma* species, wherein the composition is administered topically for a period of time necessary to detect one or more therapeutic effects, and wherein the one or more therapeutic effects persist for at least 8 weeks, at least 12 weeks, at least 16 weeks, at least 20 weeks, at least 24 weeks or more after the last administration of the composition.

A further object of the present invention is to provide the use of a composition of the invention in the manufacture of a medicament for the treatment and/or prevention of an inflammatory skin disease in a subject.

A further object of the present invention is to provide a kit for the treatment and/or prevention of an inflammatory skin disease comprising a composition, or composition for use, of the invention.

DETAILED DESCRIPTION OF THE INVENTION

Figure 1:
FIG. 1 is a picture representing Atopic Dermatitis on the lip (Cheilitis) before treatment.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise/comprising" is generally used in the sense of include/including, that is to say permitting the presence of one or more features or components. The terms "comprise(s)" and "comprising" also encompass the more restricted ones "consist(s)", "consisting" as well as "consist/consisting essentially of", respectively.

As used in the specification and claims, the singular form "a", "an" and "the" include plural references unless the context clearly dictates otherwise.

As used herein the terms "subject"/"subject in need thereof", or "patient"/"patient in need thereof" are well-recognized in the art, and, are used interchangeably herein to refer to a mammal, including dog, cat, rat, mouse, monkey, cow, horse, goat, sheep, pig, camel, and, most preferably, a human. In some cases, the subject is a subject in need of treatment or a subject with a disease or disorder. However, in other aspects, the subject can be a normal subject. The term does not denote a particular age or sex. Thus, adult and newborn subjects, whether male or female, are intended to be covered. Preferably, the subject is a human, most preferably a human suffering from an inflammatory skin disease or a human that might be at risk of suffering from an inflammatory skin disease.

The term "about," particularly in reference to a given quantity, number or percentage, is meant to encompass deviations of plus or minus ten percent (±10). For example, about 5% encompasses any value between 4.5% to 5.5%, such as 4.5, 4.6, 4.7, 4.8, 4.9, 5, 4.1, 5.2, 5.3, 5.4, or 5.5.

As used herein, "at least one" means "one or more", "two or more", "three or more", etc. For example, at least 8 weeks means 8 weeks or more i.e., 9 weeks, 10 weeks, 11 weeks, In one aspect, the invention provides a method of treatment and/or prevention of an inflammatory skin disease in a subject, said method comprising administering a composition comprising, as active ingredients, effective amounts of an extract of *Allium* species, an extract of *Citrus* species, an extract of *Paullinia* species and an extract of *Theobroma* species, wherein the composition is administered topically for a period of time necessary to detect one or more therapeutic effects.

In one aspect, the one or more therapeutic effects persist for at least 8 weeks, at least 12 weeks, at least 16 weeks, at least 20 weeks, at least 24 weeks or more after the last administration of the composition.

The term "treatment" or "treating" means any administration of a composition, pharmaceutical composition, therapeutic agent, active ingredient, compound, etc., of the disclosure to a subject for the purpose of:

(i) inhibiting the disease, that is, arresting the development of clinical symptoms;

(ii) reversing the disease, and/or (iii) relieving the disease, that is, causing the regression of clinical symptoms.

As used herein, the term "prevention" or "preventing" means any administration of a composition, pharmaceutical composition, therapeutic agent, active ingredient, compound, etc. . . . , of the disclosure to a subject for the purpose of preventing the disease, that is, causing the clinical symptoms and signs of the disease not to develop.

In the context of the present invention, the disease is inflammatory skin disease. In an aspect, the inflammatory skin disease is Atopic Dermatitis.

Preferably, the inflammatory skin disease is Atopic Dermatitis (AD).

Atopic dermatitis is considered to be a chronic relapsing inflammatory skin disease or condition. As a result, it is generally presented in 3 different clinical phases:

acute AD (a vesicular, weeping, crusting eruption);

subacute AD (dry, scaly, erythematous papules and plaques); and chronic AD (lichenification, thickening, from repeated scratching).

AD is commonly localized to the flexural surfaces of the body, anterior and lateral neck, eyelids, forehead, face, wrists, dorsa of the feet, and hands.

In addition to the clinical phases described above, the disease course of AD is not static but rather defined by a pattern. A study conducted in 2004 looked at disease course, with AD falling into 1 of 3 disease patterns: 1) persistent (19%; AD atevery follow-up until age 7 years); 2) intermittent (38%; early AD not fitting persistentor remission criteria); or 3) remission (43%; no AD after the age of 2 years) (Illi S, von Mutius E, Lau S, et al; Multicenter Allergy Study Group. The natural course of atopic dermatitis from birth to age 7 years and the association with asthma. JAllergy Clin Immunol. 2004; 113(5):925-931).

The term "effective amount" as used herein means a therapeutically effective amount of a composition, a pharmaceutical composition, a therapeutic agent, an active ingredient, a compound, etc of the disclosure, high enough to significantly positively modify the symptoms and/or condition to be treated, but low enough to avoid serious side effects (at a reasonable risk/benefit ratio), within the scope of sound medical judgment.

In the context of the present invention, the composition of the invention comprises, as active ingredients, effective amounts of an extract of *Allium* species, an extract of *Citrus* species, an extract of *Paullinia* species and an extract of *Theobroma* species active *Allium* species, an extract of *Citrus* species, an extract of *Paullinia* species and an extract of *Theobroma* species.

The term extract, or aqueous-alcoholic extract, of *Allium* species refers particularly to aqueous-alcoholic extracts and native extracts, e.g. aqueous extract, obtained from all species of the genus *Allium* (family Liliaceae) and especially *Allium cepa.*

The term extract, or aqueous-alcoholic extract, of *Citrus* species refers particularly to aqueous-alcoholic extracts and native extracts e.g. aqueous extracts, obtained from all species of the genus *Citrus* (family Rutaceae) and especially *Citrus* limon.

The term extract (atomised or not), or aqueous-alcoholic extract, of *Paullinia* species refers particularly to aqueous-alcoholic extracts and native extracts, e.g. aqueous extracts, obtained from all species of the genus *Paullinia* (family Sapindaceae) and especially *Paullinia* cupana.

The term extract (atomised or not), or aqueous-alcoholic extract, of *Theobroma* species refers particularly to aqueous-alcoholic extracts and native extracts, e.g. aqueous extracts, obtained from all species of the genus *Theobroma* (family Malvaceae) and especially *Theobroma cacao.*

In an aspect of the invention, the composition, or composition for use, of the invention is administered topically, usually on external skin surface preferably to an affected area for a period of time necessary to detect one or more therapeutic effects consisting of slowing down or arresting the development of clinical symptoms, reversing the disease and/or causing the regression of clinical symptoms.

In one aspect, clinical symptoms of AD comprise:
vesicular, weeping, crusting eruptions (acute AD);
dry, scaly, erythematous papules and plaques (subacute AD); and
chronic AD (lichenification, thickening, from repeated scratching), severe itching and pain, changes in heart rate and temperature, dehydration and nail changes (chronic AD).

The period of time necessary to detect one or more therapeutic effects is usually comprised between about 16 to about 48 weeks, preferably between about 20 to about 40 weeks, more preferably between about 20 and about 32 weeks and even more preferably about 24 weeks.

Any invasive or non-invasive method known in the art may be used to detect, monitor and/or evidence the one or more therapeutic effects described above.

In one aspect, the one or more therapeutic effects are detected, monitored and/or evidenced by, e.g.:
Skin histology;
Performing an Investigator Global Assessment (IGA), a 5-point scale, including morphological descriptions, that was developed by an expert panel to assess the severity of atopic dermatitis (Simpson E et al. 2020);
Calculating an Eczema Area and Severity Index score (EASI), a validated tool for the measurement of severity of atopic dermatitis (Leshem et al., 2015);
Determining an Itch Numeric Rating Scale (NRS), Calculating a Dermatology Life Quality Index (DLQI), or Children's Dermatology Life Quality Index (CDLQI), both are clinical assessment tools, developed by researchers at Cardiff University via research published in 1994 (Finlay et al., 1994).

In one aspect, a decrease or regression of at least about 2% or more, at least about 5% or more, at least about 10% or more, at least about 15% or more, at least about 20% or more, at least about 30% or more, at least about 40% or more, or at least about 50% or more of the clinical symptoms detected when compared to the subject's symptoms determined before starting the administration of the composition and indicates that the administration of the composition of the invention is effective.

A decrease of at least about 2% or more, at least about 5% or more, at least about 10% or more, at least about 15% or more, at least about 20% or more, at least about 30% or more, at least about 40% or more, or at least about 50% or more of the clinical symptoms detected when compared to the subject's symptoms determined after the last administration of the composition, indicates that one or more therapeutic effects are detected and persist after the stop of said topical administration.

In some aspects, the one or more therapeutic effects persist and even improves over the time.

Usually, the composition of the invention is administered topically, preferably on external skin surface of an affected area, at least once per day, at least twice per day, or more. More preferably, the composition of the invention is administered topically once per day.

Usually, a volume comprised between about 0.5 ml and 2.5 ml is applied, at least once per day, at least twice per day, or more, in order to cover the whole affected area of the subject.

In one aspect, the composition, or composition for use, of the invention comprises from about 65% to about 93% by weight of an aqueous or aqueous-alcoholic extract of *Allium* species; from about 5% to about 33% by weight of an aqueous or aqueous-alcoholic extract of *Citrus* species; from about 0.25% to about 2.5% by weight of an aqueous or aqueous-alcoholic extract of *Paullinia* species; and from about 0.25% to about 2.5% by weight of an aqueous or aqueous-alcoholic extract of *Theobroma* species.

In a preferred aspect, the composition, or composition for use, of the invention comprises from about 65% to about 93% by weight of an aqueous or aqueous-alcoholic extract of *Allium cepa*; from about 5% to about 33% by weight of an aqueous or aqueous-alcoholic extract of *Citrus limon*; from about 0.25% to about 2.5% by weight of an aqueous or aqueous-alcoholic extract of *Paullinia* cupana; and from about 0.25% to about 2.5% by weight of an aqueous or aqueous-alcoholic extract of *Theobroma cacao.*

In an even more preferred aspect, the composition, or composition for use, of the invention comprises about 87% by weight of an aqueous or aqueous-alcoholic extract of *Allium cepa*; about 12% by weight of an aqueous or aqueous-alcoholic extract of *Citrus limon*; about 0.33% by weight of an aqueous or aqueous-alcoholic extract of *Paullinia* cupana; and about 0.33% by weight of an aqueous or aqueous-alcoholic extract of *Theobroma cacao.*

In one aspect, the composition of the invention, or composition for use, further contains as excipients from about 0.05% to about 8.0% by weight of sodium chloride and from about 1% to about 40% by weight of glycerine, based on the total weight of the composition.

In one aspect, the composition of the invention, or composition for use, comprises from about 0.05% to about 8.0%, preferably from about 0.1% to about 7.0%, more preferably from about 0.4% to about 6.0%, and even more preferably from about 0.9% to about 3% by weight of sodium chloride, based on the total weight of the composition.

In one aspect, the composition of the invention, or composition for use, comprises from about 1% to about 40%, preferably from about 1.2% to about 20%, more preferably from about 1.8% to about 15% by weight of glycerine, based on the total weight of the composition.

The compositions of the invention suitable for topical administration include liquid or semi-liquid preparations suitable for penetration through the skin such as solutions, lotions, shake lotions, creams, ointments, gels, foams, transdermal patches, powders, solids, sponges, tapes, vapors, pastes, tinctures, microparticles, microcapsules, nanoparticles, liposomes, or emulsions. Preferably, the compositions of the invention suitable for topical administration are in the form of solutions or lotions.

In one aspect, the compositions of the invention are combined or co-administered with an additional therapeutic agent.

Where the inflammatory skin disease is AD, the additional therapeutic agent is selected from the group comprising microbiota replacement, new phosphodiesterase 4 (PDE4) inhibitors, specific antibodies targeting e.g., skin alarmins, histamine, substance-P or P2X3 receptors, Ig-E, various cytokines or their receptors (IL-25, IL-33, IL-1a, IL-22, IL-17C, IL-31, IL-4(&R), IL-13(&R), -5(&Ra)), and eventually systemic immunosuppressants such as JAK Inhibitors.

The present invention further contemplates the use of a composition of the invention in the manufacture of a medicament for the treatment and/or prevention of an inflammatory skin disease in a subject, comprising, administering the medicament comprising, as active ingredients, effective amounts of an extract of *Allium* species, an extract of *Citrus* species, an extract of *Paullinia* species and an extract of *Theobroma* species, wherein the composition is administered topically for a period of time necessary to detect one or more therapeutic effects.

In one aspect, the one or more therapeutic effects persist for at least 8 weeks, at least 12 weeks, at least 16 weeks, at least 20 weeks, at least 24 weeks or more after the last administration of the composition.

The invention also contemplates kits for the treatment and/or prevention of an inflammatory skin disease as described herein. In one aspect of the invention, the kit comprises a composition, or composition for use, of the invention.

The kits of the invention may also comprise a container and a label or package insert on or associated with the container. Suitable containers include, for example, bottles, vials, syringes, dispensers, a spray applicator, etc. The containers may be formed from a variety of materials such as glass or plastic.

The label or package insert may comprise instructions for use thereof. Instructions included may be affixed to packaging material or may be included as a package insert. While the instructions are typically written or printed materials they are not limited to such. Any medium capable of storing such instructions and communicating them to an end user is contemplated by this disclosure.

The present disclosure is to be considered as in all aspects illustrated and not restrictive, the scope of the invention being indicated by the appended Claims, and all changes which come within the meaning and range of equivalency are intended to be embraced therein.

Examples

Materials and Methods

An 8-year-old girl was presenting persistent atopic dermatitis on the lip (cheilitis) with intermittent acute flares. Dry skin, erythema, desquamation, and the Dennie Morgan sign associated with nocturnal pruritus complete the clinical picture (FIG. 1). Conventional approaches led to a partially favourable situation. The composition according to the invention has been introduced as an adjunctive therapy to decrease the sensation of pruritus and control skin lesions.

Results

Figure 2:
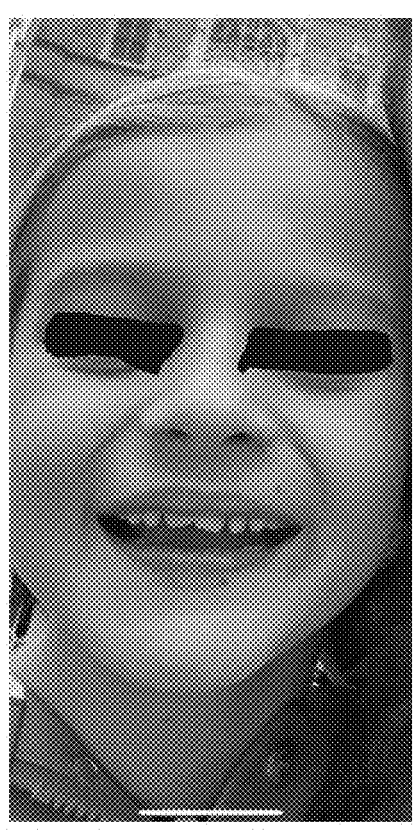
FIG. 2 is a picture representing Atopic Dermatitis on the lip (Cheilitis) after treatment.

The patient experienced immediate improvement with a significant decrease in itch, dryness, rhagades, and inflammation with 1 application daily for 5 days during one month. (FIG. 2). After that, the treatment with the composition was discontinued. The improvement experience by the patient was maintained despite discontinuation.

Discussion

Our results confirm the immediate anti-inflammatory response and long-term maintenance that allow the patient to subjectively experience disease control. Long-term steroid use, even at regular intervals, can often pose compliance and side effects problems (vasoconstriction, fragility of the skin barrier). Calcineurin inhibitors are often poorly tolerated due to the associated mast cell stimulation, especially on the lips. This preliminary work highlights the potential of the composition in the management of AD, knowing that many patients or their parents seek alternatives to standard treatment. In this case report, the composition according to the invention represents a safe, effective and well-tolerated therapeutic modality, in combination with conventional anti-inflammatory treatment or as monotherapy. However, more studies are needed to confirm its efficacy.

REFERENCES

1. Braun C, Vocanson M, Nicolas J F, Nosbaum A et al. Physiopathologie de la dermatite atopique et des autres maladies atopiques: une approche globale est-elle possible?Ann Dermatol Venereol 2020; 147:11S4-11S11.
2. Eichenfield L F, Kusari A, Han A M, Barbarot S, Deleuran M, Lio P et al. Therapeutic education in atopic dermatitis: a position paper From the International Eczema Coucil. JAAD Int 2021; 5:8-13.
3. Newsom M. Bashyam A M, Balogh E A, Feldman S R, Strowd L C et al. New and emerging systemic treatments for atopic dermatitis. Drugs 2020; 80:1041-1052.
4. Katoulis A C, Liakou A, Alevizou A, Bonovas S, Bozi E, Kontogiorgi D et al. Efficacy and safety of a topical botanical in female androgenic alopecia: a randomized single-blinded vehicle-controlled study. Skin Appendage Disord 2018; 4:160-165.
5. Liu J, Harti S, Mello A, Cauwenbergh G et al. A topical botanical lotion increases and remodels calp collagen content through longer anagen phase, opening new perspectives. Abstract 2707, J Am Acad Dermatol 2016. Hair and Nail Disorders 2016; 74 Supplement 1, AB132.
6. Chopra R, Silverberg J I. Assessing the severity of atopic dermatitis in clinical trials and practice. Clin Dermatol. 2018 September-October; 36(5):606-615.

7. Simpson E, Bissonnette R, Eichenfield L F, Guttman-Yassky E, King B, Silverberg J I, Beck L A, Bieber T, Reich K, Kabashima K, Seyger M, Siegfried E, Stingl G, Feldman S R, Menter A, van de Kerkhof P, Yosipovitch G, Paul C, Martel P, Dubost-Brama A, Armstrong J, Chavda R, Frey S, Joubert Y, Milutinovic M, Parneix A, Teixeira H D, Lin C Y, Sun L, Klekotka P, Nickoloff B, Dutronc Y, Mallbris L, Janes J M, DeLozier A M, Nunes F P, Paller A S. The Validated Investigator Global Assessment for Atopic Dermatitis (vIGA-AD): The development and reliability testing of a novel clinical outcome measurement instrument for the severity of atopic dermatitis. J Am Acad Dermatol. 2020 September; 83(3):839-846.

8. Leshem, Y. A.; Hajar, T; Hanifin, J. M.; Simpson, E. L. (2015). "What the Eczema Area and Severity Index score tells us about the severity of atopic dermatitis: An interpretability study". British Journal of Dermatology. 172 (5): 1353-7

9. Finlay, A. Y. and Khan, G. K. 1994. Dermatology Life Quality Index (DLQI)—a simple practical measure for routine clinical use. Clinical and Experimental Dermatology 19 (3), pp. 210-216.

The invention claimed is:

1. A method of treatment of atopic dermatitis in a human in need thereof consisting essentially of topically administering a composition to the human, wherein the composition consists of, as active ingredients, effective amounts of an extract of *Allium* species, an extract of Citrus species, an extract of *Theobroma* species, and an extract of Paullinia species, and excipients, wherein the extract of Paullinia species consists of an aqueous extract without alcohol, and wherein one or more therapeutic effects of the treatment persists for at least 8 weeks after the last administration of the composition.

2. The method of treatment according to claim 1, wherein the atopic dermatitis is selected from the group consisting of acute atopic dermatitis, subacute atopic dermatitis, and chronic atopic dermatitis.

3. The method of treatment according to claim 1, wherein a decrease or regression of at least about 2% or more, at least about 5% or more, at least about 10% or more, at least about 15% or more, at least about 20% or more, at least about 30% or more, at least about 40% or more, or at least about 50% or more of the clinical symptoms is detected when compared to the human's symptoms determined after the last administration of the composition.

4. The method of treatment according to claim 1, wherein a decrease or regression of at least about 2% or more, at least about 5% or more, at least about 10% or more, at least about 15% or more, at least about 20% or more, at least about 30% or more, at least about 40% or more, or at least about 50% or more of the clinical symptoms is detected when compared to the subject's symptoms determined before starting the administration of the composition.

5. The method of treatment according to claim 1, wherein the composition consists essentially of from about 65% to about 93% by weight of an aqueous or aqueous-alcoholic extract of *Allium* species; from about 5% to about 33% by weight of an aqueous or aqueous-alcoholic extract of Citrus species; from about 0.25% to about 2.5% by weight of an aqueous extract of Paullinia species; and from about 0.25% to about 2.5% by weight of an aqueous or aqueous-alcoholic extract of *Theobroma* species.

6. The method of treatment according to claim 1, wherein the composition consists essentially of from about 65% to about 93% by weight of an aqueous or aqueous-alcoholic extract of *Allium cepa*; from about 5% to about 33% by weight of an aqueous or aqueous-alcoholic extract of *Citrus limon*; from about 0.25% to about 2.5% by weight of an aqueous extract of Paullinia cupana; and from about 0.25% to about 2.5% by weight of an aqueous or aqueous-alcoholic extract of *Theobroma cacao*.

7. The method of treatment according to claim 6, wherein the composition consists essentially of about 87% by weight of an aqueous or aqueous-alcoholic extract of *Allium cepa*; about 12% by weight of an aqueous or aqueous-alcoholic extract of *Citrus limon*; about 0.33% by weight of an aqueous extract of Paullinia cupana; and about 0.33% by weight of an aqueous or aqueous-alcoholic extract of *Theobroma cacao*.

8. The method of treatment according to claim 1, wherein the composition further consists essentially of from about 0.05% to about 8.0% by weight of sodium chloride and from about 1% to about 40% by weight glycerine based on the total weight of the composition.

9. The method of treatment according to claim 8, wherein the composition consists essentially of from about 0.1% to about 7%, or from about .4% to about 6%, or from about 1.2% to about 20%, or from about 1.8% to about 15% by weight of glycerine, based on the total weight of the composition.

10. The method of treatment according to claim 1, wherein the composition is administered topically on the skin of the human to an affected area of the human.

11. The method of treatment according to claim 1, wherein the composition is administered at least once a day.

12. The method of treatment according to claim 1, wherein the composition is administered for about 16 to 48 weeks.

13. The method of treatment according to claim 12, wherein the composition is administered for about 20 to 40 weeks.

14. The method of treatment according to claim 1, wherein the one or more therapeutic effects of the treatment persists for at least 12 weeks after the last administration of the composition.

15. The method of treatment according to claim 14, wherein the one or more therapeutic effects of the treatment persists for at least 16 weeks after the last administration of the composition.

* * * * *